United States Patent
Small et al.

(10) Patent No.: US 11,884,614 B2
(45) Date of Patent: Jan. 30, 2024

(54) NORMAL ALPHA OLEFIN SYNTHESIS USING DECARBONYLATIVE OLEFINATION

(71) Applicant: Chevron Phillips Chemical Company LP, The Woodlands, TX (US)

(72) Inventors: Brooke L. Small, Kingwood, TX (US); Michael S. Webster-Gardiner, Humble, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 103 days.

(21) Appl. No.: 17/824,960

(22) Filed: May 26, 2022

(65) Prior Publication Data

US 2023/0382825 A1    Nov. 30, 2023

(51) Int. Cl.
| | |
|---|---|
| *C07C 5/03* | (2006.01) |
| *C07C 45/50* | (2006.01) |
| *C07C 1/207* | (2006.01) |
| *B01J 31/28* | (2006.01) |
| *B01J 23/44* | (2006.01) |
| *C07C 1/24* | (2006.01) |

(52) U.S. Cl.
CPC .............. *C07C 5/03* (2013.01); *B01J 23/44* (2013.01); *B01J 31/28* (2013.01); *C07C 1/2076* (2013.01); *C07C 1/24* (2013.01); *C07C 45/505* (2013.01); *C07C 2523/44* (2013.01)

(58) Field of Classification Search
CPC ........ C07C 5/03; C07C 45/505; C07C 1/2076
See application file for complete search history.

(56) References Cited

U.S. PATENT DOCUMENTS

| | | | |
|---|---|---|---|
| 5,093,535 | A | 3/1992 | Harrison |
| 7,196,230 | B2 | 3/2007 | Peng |
| 9,809,519 | B1 | 11/2017 | Lotz |
| 10,071,937 | B2 | 9/2018 | Millet |
| 10,183,899 | B2 | 1/2019 | Bischof |
| 10,435,334 | B2 | 10/2019 | Bischof |
| 10,723,672 | B2 | 7/2020 | Bischof |

FOREIGN PATENT DOCUMENTS

| | | |
|---|---|---|
| WO | 2003024910 A1 | 3/2003 |
| WO | 2021126421 A1 | 6/2021 |

OTHER PUBLICATIONS

International Search Report and Written Opinion issued in corresponding PCT Application No. PCT/US2023/066584, dated Aug. 23, 2023, 12 pp.
Ainembabazi, et al., "Decarbonylative Olefination of Aldehydes to Alkenes", J. Am. Chem. Soc., 2020, 142, 696-699.
Behr, et al. "Highly Selective Tandem Isomerization-Hydroformylation Reaction of trans-4-octene to n-normal with Rhodium-BIPHEPOS Catalysis." Journal of Molecular Catalysis A Chemical, 206, 2003. pp. 179-184.
Borner, Isomerization-hydroformylation tandem reactions, ACS Catal. 2014, 4, 1706-24.
Chetty, et al. "Continuous Flow Preferential Hydrogenation of an Octanal/Octene Mixture Using Cu/Al2O3 Catalysts." ACS Omega 2018, 3, 7911-7924.
Jameel, et al. "Solvent Effects in Hydroformylation of Long-Chain Olefins." Molecular Catalysis, 503, 2021, 111429, Abstract. http://doi.org/10.106/j.mcat.2021.111429. 2021.
Jorke et al., Hydroformylation and tandem isomerization-hydroformylation of n-decenes using a rhodim-BiPhePhos catalyst: Kinetic modeling, reaction network analysis, and optimal reaction control, Chemical Engineering Journal, Dec. 12, 2016.
Kelly. "Process Economics Program—Review Dec. 2014: Octene-1 by Sasol Heptene-1 Hydroformylation Technology." IHS Chemical. Ihs.com/chemical. Aug. 2014. pp. 1-54.
Kim et al., Production of linear alpha-olefin 1-octene via dehydration . . . Fuel, 256, (2019) 115957.
Vasseur, et al. "Remote Functionalization Through Alkene Isomerization." Nature Chemistry. Feb. 10, 2016. pp. 209-219.
Vogl, Highly Selective Hydroformylation . . . , J. Mol. Cat. A: Chem. 232 (2005) 41-44.
Yan, et al. "A Tetraphosphorus Ligand for Highly Regioselective Isomerization-Hydroformylation of Internal Olefins." Abstract. J. Am. Society. vol. 128, No. 50. 2006.

*Primary Examiner* — Sikarl A Witherspoon
(74) *Attorney, Agent, or Firm* — Merchant & Gould P.C.

(57) ABSTRACT

An alpha olefin synthesis process includes (i) subjecting a first normal alpha olefin to hydroformylation in the presence of carbon monoxide and hydrogen to form a first linear aldehyde, (ii) subjecting the first linear aldehyde to decarbonylative olefination to form a linear internal olefin, (iii) subjecting the linear internal olefin to isomerization-hydroformylation in the presence of carbon monoxide and hydrogen to form a second linear aldehyde, and (iv) subjecting the second linear aldehyde to hydrogenation to form a linear alcohol followed by dehydration to form a second normal alpha olefin, or subjecting the second linear aldehyde to combined hydrogenation-dehydration in a single step to form a second normal alpha olefin. Using this process, for example, ethylene can be converted to 1-hexene, and 1-butene can be converted to 1-decene.

21 Claims, 1 Drawing Sheet

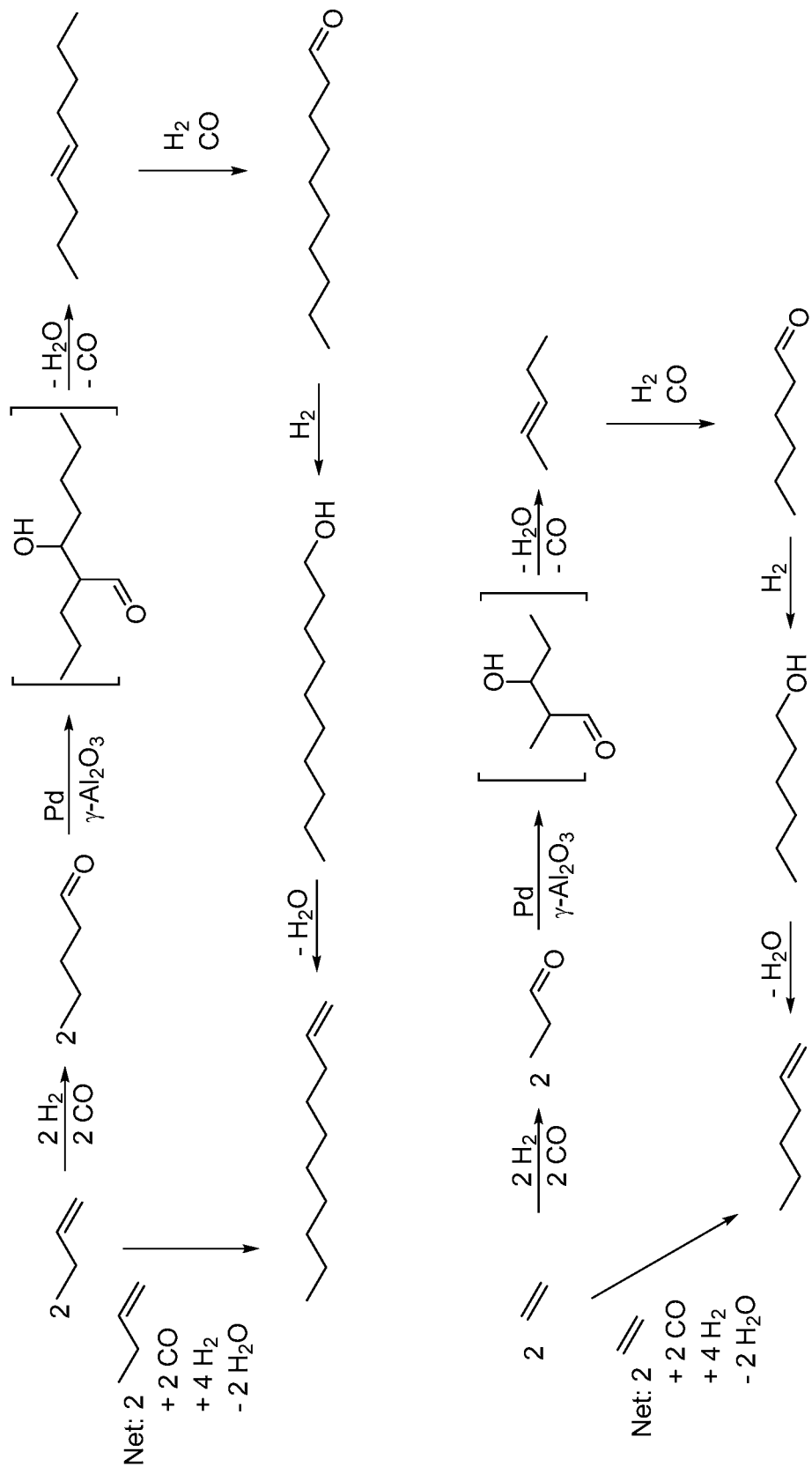

NORMAL ALPHA OLEFIN SYNTHESIS USING DECARBONYLATIVE OLEFINATION

FIELD OF THE INVENTION

The present invention relates generally to processes for producing normal alpha olefins in a multistep synthesis scheme that can include a hydroformylation step, a decarbonylative olefination step, an isomerization-hydroformylation step, a hydrogenation step, and a dehydration step.

BACKGROUND OF THE INVENTION

The synthesis of specific carbon number normal alpha olefins—in particular, 1-hexene, 1-octene, and 1-decene—is of significant importance in the chemical industry. However, with current catalysts and reaction processes, it is difficult to selectively produce only the desired carbon number alpha olefin fraction rather than a complex mixture of olefin products. It would be beneficial to develop new ways to produce specific normal alpha olefins having a specific carbon number. Accordingly, it is to these ends that the present invention is generally directed.

SUMMARY OF THE INVENTION

This summary is provided to introduce a selection of concepts in a simplified form that are further described herein. This summary is not intended to identify required or essential features of the claimed subject matter. Nor is this summary intended to be used to limit the scope of the claimed subject matter.

A process disclosed and described herein can comprise (i) subjecting a first normal alpha olefin having the structure $(C)_n$—C=C to hydroformylation in the presence of carbon monoxide and hydrogen to form a first composition comprising a first linear aldehyde having the structure $C(C)_{n+1}CH(=O)$, (ii) subjecting the first linear aldehyde to decarbonylative olefination to form a second composition comprising a $C_{2n+5}$ linear internal olefin, (iii) subjecting the linear internal olefin to isomerization-hydroformylation in the presence of carbon monoxide and hydrogen to form a third composition comprising a second linear aldehyde having the structure $C(C)_{2n+4}CH(=O)$, and (iv-a) subjecting the second linear aldehyde to hydrogenation-dehydration to form a product composition comprising a second normal alpha olefin having the structure $(C)_{2n+4}$—C=C, or (iv-b1) subjecting the second linear aldehyde to hydrogenation to form a fourth composition comprising a linear alcohol having the structure $C(C)_{2n+4}C(OH)$, and (iv-b2) subjecting the linear alcohol to dehydration to form a product composition comprising a second normal alpha olefin having the structure $(C)_{2n+4}$—C=C. In this process, n is an integer that can range from 0 to 30.

In one aspect of the disclosed process, the first normal alpha olefin can comprise ethylene and the second normal alpha olefin can comprise 1-hexene. In another aspect, the first normal alpha olefin can comprise propylene and the second normal alpha olefin can comprise 1-octene. In yet another aspect, the first normal alpha olefin can comprise 1-butene and the second normal alpha olefin can comprise 1-decene.

Both the foregoing summary and the following detailed description provide examples and are explanatory only. Accordingly, the foregoing summary and the following detailed description should not be considered to be restrictive. Further, features or variations can be provided in addition to those set forth herein. For example, certain aspects can be directed to various feature combinations and sub-combinations described in the detailed description.

BRIEF DESCRIPTION OF THE FIGURE

The following FIGURE forms part of the present specification and is included to further demonstrate certain aspects of the present invention. The invention may be better understood by reference to the FIGURE in combination with the detailed description.

The FIGURE illustrates reaction schemes for the conversion of 1-butene to 1-decene and the conversion of ethylene to 1-hexene in accordance with aspects of the present disclosure.

While the inventions disclosed herein are susceptible to various modifications and alternative forms, only a few specific aspects have been shown by way of example in the drawing and described in detail below. The FIGURE and detailed descriptions of these specific aspects are not intended to limit the breadth or scope of the inventive concepts or the appended claims in any manner. Rather, the FIGURE and detailed descriptions are provided to illustrate the inventive concepts to a person of ordinary skill in the art and to enable such person to make and use the inventive concepts.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and/or feature disclosed herein, all combinations that do not detrimentally affect the designs, compositions, processes, and/or methods described herein are contemplated with or without explicit description of the particular combination. Additionally, unless explicitly recited otherwise, any aspect and/or feature disclosed herein can be combined to describe inventive features consistent with the present disclosure.

In this disclosure, while processes are described in terms of "comprising" various steps, the processes also can "consist essentially of" or "consist of" the various steps, unless stated otherwise. The terms "a," "an," and "the" are intended to include plural alternatives, e.g., at least one, unless otherwise specified. For instance, the disclosure of "a first normal alpha olefin" or is meant to encompass one, or combinations of more than one, first normal alpha olefin, unless otherwise specified.

Generally, groups of elements are indicated using the numbering scheme indicated in the version of the periodic table of elements published in Chemical and Engineering News, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; and a general reference to a butyl group includes an n-butyl group, a sec-butyl group, an iso-butyl group, and a t-butyl group.

The term "subjecting" is used herein to describe process steps in which the materials are contacted or combined together in any order, in any manner, and for any length of time, unless otherwise specified. For example, the materials can be blended, mixed, slurried, dissolved, reacted, treated, impregnated, compounded, or otherwise contacted or combined in some other manner or by any suitable method or technique.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates that the presence of one or more halogen atoms replacing an equivalent number of hydrogen atoms in the hydrocarbon). Likewise, the term "alkane" refers to a saturated hydrocarbon compound.

The term "olefin" refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s). The term "alpha olefin" refers to any olefin that has a carbon-carbon double bond between the first and second carbon atom of the longest contiguous chain of carbon atoms. The term "alpha olefin" includes linear and branched alpha olefins and alpha olefins which can have more than one non-aromatic carbon-carbon double bond, unless expressly stated otherwise. The term "normal alpha olefin" refers to a linear aliphatic hydrocarbon mono-olefin having a carbon-carbon double bond between the first and second carbon atoms. The term "linear internal olefin" refers to a linear aliphatic hydrocarbon mono-olefin having a double bond that is not between the first and second carbon atoms.

Various numerical ranges are disclosed herein. When a range of any type is disclosed or claimed, the intent is to disclose or claim individually each possible number that such a range could reasonably encompass, including end points of the range as well as any sub-ranges and combinations of sub-ranges encompassed therein, unless otherwise specified. As a representative example, the present disclosure recites that the molar ratio of carbon monoxide to hydrogen in step (i)—or in step (iii)—of the process can be in certain ranges. By a disclosure that the molar ratio can be in a range from 5:1 to 1:5, the intent is to recite that the molar ratio can be any ratio in the range and, for example, can include any range or combination of ranges from 5:1 to 1:5, such as from 2:1 to 1:2, or from 1.5:1 to 1:1.5, and so forth. Likewise, all other ranges disclosed herein should be interpreted in a manner similar to this example.

In general, an amount, size, formulation, parameter, range, or other quantity or characteristic is "about" or "approximate" whether or not expressly stated to be such. Whether or not modified by the term "about" or "approximately," the claims include equivalents to the quantities or characteristics.

Although any methods and materials similar or equivalent to those described herein can be used in the practice or testing of the invention, the typical methods and materials are herein described.

All publications and patents mentioned herein are incorporated herein by reference in their entirety for the purpose of describing and disclosing, for example, the constructs and methodologies that are described in the publications and patents, which might be used in connection with the presently described invention.

DETAILED DESCRIPTION OF THE INVENTION

Processes for producing normal alpha olefins are disclosed herein and, in particular, atom efficient processes for converting normal alpha olefins into higher carbon number normal alpha olefins. Beneficially, these processes offer high carbon conservation and low by-product formation, and can utilize Syngas as a reactant in two separate steps of the process.

Normal Alpha Olefin Synthesis

Aspects of this invention are directed to processes that can comprise (or consist essentially of, or consist of) (i) subjecting a first normal alpha olefin having the structure $(C)_n$—C=C to hydroformylation in the presence of carbon monoxide and hydrogen to form a first composition comprising a first linear aldehyde having the structure $C(C)_{n+1}CH(=O)$, (ii) subjecting the first linear aldehyde to decarbonylative olefination to form a second composition comprising a $C_{2n+5}$ linear internal olefin, (iii) subjecting the linear internal olefin to isomerization-hydroformylation in the presence of carbon monoxide and hydrogen to form a third composition comprising a second linear aldehyde having the structure $C(C)_{2n+4}CH(=O)$, and (iv-a) subjecting the second linear aldehyde to hydrogenation-dehydration to form a product composition comprising a second normal alpha olefin having the structure $(C)_{2n+4}$—C=C, or (iv-b1) subjecting the second linear aldehyde to hydrogenation to form a fourth composition comprising a linear alcohol having the structure $C(C)_{2n+4}C(OH)$, and (iv-b2) subjecting the linear alcohol to dehydration to form a product composition comprising a second normal alpha olefin having the structure $(C)_{2n+4}$—C=C. In this process, n is an integer that can range from 0 to 30.

Generally, the features of this process (e.g., the hydroformylation step, the decarbonylative olefination step, the isomerization-hydroformylation step, the combined hydrogenation-dehydration step, the hydrogenation step, and the dehydration step, among other features) are independently described herein and these features can be combined in any combination to further describe the normal alpha olefin synthesis process. Moreover, additional process steps can be performed before, during, and/or after any of the steps of this process, unless stated otherwise.

As described herein, n can be integer that ranges from 0 to 30. In one aspect consistent with invention, n can be an integer from 0 to 18, while in another aspect, n can be an integer from 0 to 12. Yet, in another aspect, n can be an integer from 0 to 8, and in still another aspect, n can be an integer from 0 to 6. For example, n can be equal to 0, equal to 1, equal to 2, equal to 3, equal to 4, equal to 5, equal to 6, and so forth.

In some aspects of this invention, the first normal alpha olefin can comprise (or consist essentially of, or consist of) ethylene, propylene, 1-butene, 1-pentene, 1-hexene, 1-heptene, 1-octene, 1-nonene, 1-decene, 1-dodecene, 1-tetradecene, 1-hexadecene, 1-octadecene, or any combination thereof. For instance, the first normal alpha olefin can comprise (or consist essentially of, or consist of) ethylene; alternatively, propylene; alternatively, 1-butene; alternatively, 1-pentene; alternatively, 1-hexene; alternatively, 1-heptene; alternatively, 1-octene; alternatively, 1-nonene; alternatively, 1-decene; alternatively, 1-dodecene; alternatively, 1-tetradecene; alternatively, 1-hexadecene; or alternatively, 1-octadecene. In other aspects, the first normal alpha olefin can comprise (or consist essentially of, or consist of) ethylene, propylene, 1-butene, 1-pentene, 1-hexene, 1-heptene, 1-octene, or any combination thereof.

In one aspect of this invention, the first normal alpha olefin can comprise (or consist essentially of, or consist of) ethylene, and the second normal alpha olefin can comprise (or consist essentially of, or consist of) 1-hexene. In another aspect, the first normal alpha olefin can comprise (or consist essentially of, or consist of) propylene, and the second normal alpha olefin can comprise (or consist essentially of, or consist of) 1-octene. In another aspect, the first normal alpha olefin can comprise (or consist essentially of, or consist of) 1-butene, and the second normal alpha olefin can comprise (or consist essentially of, or consist of) 1-decene. In another aspect, the first normal alpha olefin can comprise (or consist essentially of, or consist of) 1-pentene, and the second normal alpha olefin can comprise (or consist essentially of, or consist of) 1-dodecene. In another aspect, the first normal alpha olefin can comprise (or consist essentially of, or consist of) 1-hexene, and the second normal alpha olefin can comprise (or consist essentially of, or consist of) 1-tetradecene. In yet another aspect, the first normal alpha olefin can comprise (or consist essentially of, or consist of) 1-heptene, and the second normal alpha olefin can comprise (or consist essentially of, or consist of) 1-hexadecene. In still another aspect, the first normal alpha olefin can comprise (or consist essentially of, or consist of) 1-octene, and the second normal alpha olefin can comprise (or consist essentially of, or consist of) 1-octadecene.

The integer n, the first normal alpha olefin, and the second normal alpha olefin are described herein and their features can be utilized without limitation to further describe the normal alpha olefin synthesis processes disclosed herein. Other suitable values for the integer n and selections for the first normal alpha olefin and the second normal alpha olefin are readily apparent from this disclosure.

Step (i) of the process disclosed herein often is referred to as the hydroformylation step, and in this step, the first normal alpha olefin having the structure $(C)_n$—C=C can be subjected to hydroformylation in the presence of carbon monoxide and hydrogen to form a first composition comprising a first linear aldehyde having the structure $C(C)_{n+1}CH(=O)$. Thus, in an aspect, this hydroformylation step can convert a first normal alpha olefin, such as ethylene or 1-butene, to a first linear aldehyde, such as propanal or 1-pentanal, respectively. Any suitable hydroformylation catalyst systems for step (i) and any suitable conditions for the hydroformylation reaction in step (i) can be employed, as would be recognized by those skilled in the art in view of this disclosure, and for instance, Behr at al., Journal of Molecular Catalysis A: Chemical 206 (2003), 179-184; Vogl at al., Journal of Molecular Catalysis A: Chemical 232 (2005), 41-44; Jorke et al., Chemical Engineering Journal, Dec. 12, 2016, 1-34; Peng et al., U.S. Pat. No. 7,196,230; and Yan et al., JACS 2006, 128, 16058-16061.

While not being limited thereto, the hydroformylation in step (i) can utilize a rhodium-based catalyst system. In such aspects, the rhodium-based catalyst system can include rhodium and a phosphorus-containing ligand, and the elemental ratio of Rh:P often can range from 1:1 to 1:15, and more often, the elemental ratio of Rh:P falls within a range from 1:2 to 1:10, or from 1:2 to 1:6, and the like. The particular phosphorus-containing ligand in not particularly limited, although BiPhePhos (CAS Number 121627-17-6) is well-suited for use in rhodium-based catalyst systems employed in hydroformylation reactions.

In one aspect, the molar ratio of the first normal alpha olefin in step (i) to rhodium in the rhodium-based catalyst system can fall within a range from 100:1 to 500,000:1, while in another aspect, the molar ratio of the first normal alpha olefin to rhodium can range from 100:1 to 10,000:1, and in yet another aspect, the molar ratio of the first normal alpha olefin to rhodium can range from 100:1 to 1000:1. As those skilled in the art would readily recognize, the alpha olefin to rhodium molar ratio can change as the hydroformylation reaction proceeds. Accordingly, these ranges of molar ratios are meant to encompass the initial ratio as well as any molar ratio of the first normal alpha olefin to rhodium encountered as the hydroformylation reaction proceeds.

Additionally, the molar ratio of carbon monoxide to hydrogen ($H_2$) in the hydroformylation reaction of step (i) often ranges from 5:1 to 1:5 or from 2:1 to 1:2 in some aspects, and from 1.5:1 to 1:1.5 or from 1.1:1 to 1:1.1 in other aspects. The source of carbon monoxide and hydrogen used in step (i) is not limited, but in a particular aspect of this invention, the source of carbon monoxide and hydrogen in step (i) can be Syngas. As would be recognized by those skilled in the art, Syngas is a mixture containing predominately carbon monoxide and hydrogen. Syngas also can contain carbon dioxide and methane in lesser amounts.

The temperature and pressure conditions used for the hydroformylation step are not particularly limited. Generally, however, the hydroformylation temperature can be in a range from 80 to 200° C.; alternatively, from 80 to 160° C.; or alternatively, from 100 to 130° C. The hydroformylation pressure can be in range from 5 to 70 bar; alternatively, from 10 to 50 bar; or alternatively, from 20 to 45 bar. These temperature and pressure ranges also are meant to encompass circumstances where step (i) is conducted at a series of different temperatures and pressures instead of at a single fixed temperature and a single fixed pressure, wherein at least one temperature and pressure fall within the respective ranges.

If desired, and depending upon the first normal alpha olefin (e.g., its carbon number), the hydroformylation temperature, and the hydroformylation pressure, among other considerations, the hydroformylation reaction of step (i) optionally can be performed in a diluent. Illustrative and non-limiting examples of diluents that can be used include toluene, propylene carbonate, dimethylformamide, dodecane, and the like, as well as a mixture or combination thereof (see, e.g., Stein, Molecular Catalysis 503, 2021, 111429). Any suitable amount of the diluent, relative to the amount of the first normal alpha olefin, can be used.

Typically, using hydroformylation in step (i) produces both linear and branched aldehydes but, primarily produces linear aldehydes. Thus, the first composition produced via the hydroformylation of step (i) can include the first linear aldehyde, having the structure $C(C)_{n+1}CH(=O)$, and a small amount of branched aldehydes, and if used, a diluent. Optionally, prior to step (ii), the process can further comprise a step of isolating an aldehyde composition comprising at least 85 mol %, at least 90 mol %, at least 93 mol %, or at least 96 mol % of the first linear aldehyde from the first composition. Any suitable technique can be used, such as extraction, filtration, evaporation, distillation, and the like, as well as any combination thereof.

Referring now to step (ii) of the process, the first linear aldehyde formed in step (i) is subjected to decarbonylative olefination to form a second composition comprising a $C_{2n+5}$ linear internal olefin. Step (ii) of the process often is referred to as the decarbonylative olefination step. Thus, in step (ii), decarbonylative olefination can convert a first linear aldehyde, such as propanal or 1-pentanal, to a linear internal olefin, such as 2-pentene or 4-nonene, respectively. Any suitable decarbonylative olefination catalyst systems for step (ii) and any suitable conditions for the decarbonylative olefination reaction in step (ii) can be employed, as would be recognized by those skilled in the art in view of this disclosure, and for instance, Ainembabazi at al., Journal of the American Chemical Society 2020, 142, 696-699.

While not being limited thereto, the decarbonylative olefination in step (ii) can utilize a palladium-based catalyst system. In such aspects, the palladium-based catalyst system can be a supported palladium catalyst, non-limiting of examples of which can include Pd/hydrotalcite, Pd/alumina, Pd/gamma alumina, Pd/silica, Pd/carbon, or Pd/magnesia, and the like, as well as combinations thereof. Any suitable amount of palladium can be used, such as from 0.01 to 10 mol %, and more often from 0.05 to 5 mol %, or from 0.05 to 1 mol %, and the like.

Reaction conditions used for the decarbonylative olefination step are not particularly limited. However, in one aspect, the decarbonylative olefination reaction temperature can be in a range from 80 to 200° C., while in another aspect, the reaction temperature can range from 100 to 190° C., and in yet another aspect, the reaction temperature can range from 150 to 180° C. These temperature ranges also are meant to encompass circumstances where step (ii) is conducted at a series of different temperatures instead of at a single fixed temperature, wherein at least one temperature falls within the respective temperature ranges.

Decarbonylative olefination in step (ii) produces a desired linear internal olefin, but also can produce carbon monoxide, water, or both. Thus, the second composition resulting from step (ii) can comprise the linear internal olefin, carbon monoxide, and water. Therefore, prior to step (iii), the process optionally can further comprise a step of isolating an internal olefin composition comprising at least 85 mol %, at least 90 mol %, at least 93 mol %, or at least 96 mol % of the linear internal olefin from the second composition. As above, any suitable technique can be used, such as extraction, filtration, evaporation, distillation, and the like, as well as any combination thereof.

Referring now to step (iii) of the process, the linear internal olefin formed in step (ii) is subjected to isomerization-hydroformylation in the presence of carbon monoxide and hydrogen to form a third composition comprising a second linear aldehyde having the structure $C(C)_{2n+4}CH(=O)$. Step (iii) of the process often is referred to as the isomerization-hydroformylation step. In step (iii), isomerization-hydroformylation can convert a linear internal olefin, such as 2-pentene or 4-nonene, to a second linear aldehyde, such as 1-hexanal or 1-decanal, respectively.

Isomerization-hydroformylation step (iii) of the process can utilize any of the catalyst systems and reaction conditions disclosed herein for hydroformylation step (i) of the process, and as disclosed in the Behr, Vogl, Jorke, Peng, and Yan references. Thus, the isomerization-hydroformylation in step (iii) can utilize a rhodium-based catalyst system, which can include rhodium and a phosphorus-containing ligand (such as BiPhePhos) at any elemental ratio of Rh:P from 1:1 to 1:15.

Also similar to step (i), the molar ratio of carbon monoxide to hydrogen ($H_2$) in the isomerization-hydroformylation reaction of step (iii) can be any molar ratio from 5:1 to 1:5, and the source of carbon monoxide and hydrogen used in step (iii) can be Syngas, while not limited thereto. Likewise, the temperature and pressure conditions utilized for the isomerization-hydroformylation step encompass the same temperature and pressure conditions for step (i), and any temperature ranging from 80 to 200° C. and any pressure ranging from 5 to 70 bar can be utilized. Further, the isomerization-hydroformylation reaction of step (iii) can be performed in any suitable diluent and using any amount of the diluent, analogous to step (i).

In one aspect, the molar ratio of the linear internal olefin in step (iii) to rhodium in the rhodium-based catalyst system can fall within a range from 100:1 to 500,000:1, while in another aspect, the molar ratio of the linear internal olefin to rhodium can range from 100:1 to 10,000:1, and in yet another aspect, the molar ratio of the linear internal olefin to rhodium can range from 100:1 to 1000:1. As those skilled in the art would readily recognize, the linear internal olefin to rhodium molar ratio can change as the isomerization-hydroformylation reaction proceeds. Accordingly, these ranges of molar ratios are meant to encompass the initial ratio as well as any molar ratio of the linear internal olefin to rhodium encountered as the isomerization-hydroformylation reaction proceeds.

The isomerization-hydroformylation in step (iii) produces both linear and branched aldehydes, but primarily produces linear aldehydes. Thus, the third composition produced via the isomerization-hydroformylation of step (iii) can include the second linear aldehyde having the structure $C(C)_{2n+4}CH(=O)$ and a small amount of branched aldehydes, and if used, a diluent. Optionally, prior to step (iv-a) or (iv-b1), the process can further comprise a step of isolating a second aldehyde composition comprising at least 85 mol %, at least 90 mol %, at least 93 mol %, or at least 96 mol % of the second linear aldehyde from the third composition. This can be accomplished via any suitable technique, and non-limiting examples include extraction, filtration, evaporation, distillation, and the like. Combinations of two or more techniques can be used.

Once the second linear aldehyde (with the structure $C(C)_{2n+4}CH(=O)$) has been formed, the normal alpha olefin synthesis process disclosed herein has two alternative pathways to form the second normal alpha olefin (with the structure $(C)_{2n+4}$—C=C). In one pathway (via step (iv-a)), the second linear aldehyde is subjected to hydrogenation-dehydration, a combined hydrogenation and dehydration in a single combined step, to form a product composition comprising the second normal alpha olefin having the structure $(C)_{2n+4}$—C=C. In the other pathway, the second linear aldehyde is (iv-b1) subjected to hydrogenation to form a fourth composition comprising a linear alcohol having the structure $C(C)_{2n+4}C(OH)$, and then the linear alcohol is (iv-b2) subjected to dehydration to form a product composition comprising the second normal alpha olefin having the structure $(C)_{2n+4}$—C=C.

Referring now to the latter pathway and steps (iv-b1) and (iv-b2) of the process, step (iv-b1) of the process often is referred to as the hydrogenation step and step (iv-b2) often is referred to as the dehydration step. Thus, in step (iv-b1), hydrogenation can convert a second linear aldehyde, such as 1-hexanal or 1-decanal, to a linear alcohol, such as 1-hexanol or 1-decanol, respectively. Next, in step (iv-b2), dehydration can convert the linear alcohol, such as 1-hexanol or 1-decanol, to a second normal alpha olefin, such as 1-hexene or 1-decene, respectively.

Referring first to step (iv-b1), any suitable hydrogenation catalyst systems for step (iv-b1) and any suitable conditions for the hydrogenation reaction in step (iv-b1) can be employed, as would be recognized by those skilled in the art in view of this disclosure, and for instance, Chetty et al., American Chemical Society Omega 2018, 3, 7911-7924; and U.S. Pat. No. 5,093,535.

While not being limited thereto, the hydrogenation in step (iv-b1) can utilize a copper-based catalyst system. One such copper-based catalyst system can comprise Cu/alumina with any suitable amount of copper, such as from 1 to 35 wt. % copper based on the weight of the supported catalyst. In some aspects, the amount of copper in the Cu/alumina catalyst falls within a range from 2 to 30 wt. %, or from 5 to 25 wt. %, and the like.

The temperature and pressure conditions used for the hydrogenation step are not particularly limited. Generally, however, the hydrogenation temperature can be in a range from 80 to 200° C.; alternatively, from 90 to 190° C.; or alternatively, from 100 to 180° C. The hydrogenation pressure can be in range from 10 to 70 bar; alternatively, from 20 to 50 bar; or alternatively, from 25 to 45 bar. These temperature and pressure ranges also are meant to encompass circumstances where step (iv-b1) is conducted at a series of different temperatures and pressures instead of at a single fixed temperature and a single fixed pressure, wherein at least one temperature and pressure fall within the respective ranges.

In one aspect, the molar ratio of hydrogen ($H_2$) to second linear aldehyde in step (iv-b1) can fall within a range from 0.5:1 to 5:1, while in another aspect, the molar ratio of hydrogen to the second linear aldehyde can range from 0.75:1 to 3:1, and in yet another aspect, the molar ratio of hydrogen to the second linear aldehyde can range from 1:1 to 2:1. As those skilled in the art would readily recognize, the molar ratio of hydrogen ($H_2$) to second linear aldehyde can change as the hydrogenation reaction proceeds. Accordingly, these ranges of molar ratios are meant to encompass the initial ratio as well as any molar ratio of the hydrogen to second linear aldehyde encountered as the hydrogenation reaction proceeds.

The hydrogenation in step (iv-b1) primarily produces a desired linear alcohol, although other by-products of the hydrogenation reaction can be formed. Thus, optionally, prior to step (iv-b2), the process can further comprise a step of isolating an alcohol composition comprising at least 85 mol %, at least 90 mol %, at least 93 mol %, or at least 96 mol % of the linear alcohol from the fourth composition. As described herein, this can be accomplished via any suitable technique, and non-limiting examples include extraction, filtration, evaporation, distillation, and the like, as well as any combination thereof.

Referring now to step (iv-b2), any suitable dehydration catalyst systems for step (iv-b2) and any suitable conditions for the dehydration reaction in step (iv-b2) can be employed, as would be recognized by those skilled in the art in view of this disclosure, and for instance, Kim et al., Fuel 256 (2019), 115957, 1-8; and Millet et al., U.S. Pat. No. 10,071,937 (2018).

While not being limited thereto, the dehydration in step (iv-b2) in one aspect can utilize an alumina-based catalyst system, and in another aspect, the dehydration in step (iv-b2) can utilize a metal phosphate-based catalyst system. If the alumina-based catalyst system is utilized, the alumina can be calcined at any suitable temperature prior to step (iv-b2). Typical ranges for the calcining temperature include, for instance, from 100 to 1200° C., from 250 to 1000° C., or from 400 to 600° C., and the like. If the metal phosphate-based catalyst system is utilized, suitable metals include lanthanum, neodymium, gadolinium, samarium, and the like, among others.

Reaction conditions used for the dehydration step are not particularly limited. However, in one aspect, the dehydration reaction temperature can be in a range from 200 to 500° C., while in another aspect, the reaction temperature can range from 250 to 450° C., and in yet another aspect, the reaction temperature can range from 300 to 400° C. These temperature ranges also are meant to encompass circumstances where step (iv-b2) is conducted at a series of different temperatures instead of at a single fixed temperature, wherein at least one temperature falls within the respective temperature ranges.

Dehydration in step (iv-b2) produces a desired second normal alpha olefin, but also can produce water. Thus, the product composition resulting from step (iv-b2) can comprise the second normal alpha olefin and water. Therefore, the process can further comprise a step of purifying the product composition to isolate an alpha olefin composition comprising at least 85 mol %, at least 90 mol %, at least 93 mol %, or at least 96 mol % of the second normal alpha olefin. Suitable techniques include, for instance, extraction, filtration, evaporation, distillation, and the like, as well as combinations thereof.

Referring now to pathway via step (iv-a), the second linear aldehyde is subjected to a combined (single step) hydrogenation-dehydration to form a product composition comprising a second normal alpha olefin having the structure $(C)_{2n+4}$—C=C. Step (iv-a) of the process often is referred to as the hydrogenation-dehydration step. In step (iv-a), hydrogenation-dehydration can convert the second linear aldehyde, such as 1-hexanal or 1-decanal, to a second normal alpha olefin, such as 1-hexene or 1-decene, respectively.

Any suitable hydrogenation-dehydration catalyst systems for step (iv-a) and any suitable conditions for the hydrogenation-dehydration reaction in step (iv-a) can be employed, as would be recognized by those skilled in the art in view of this disclosure, and the related hydrogenation process and catalyst systems and dehydration process and catalyst systems described above. It is advantageous if this step disfavors complete hydrogenation, and thus forms a product composition containing less than 10 wt. %, or less than 5 wt. %, of alkanes such as n-alkanes; thus, the unsaturated second normal alpha olefin is produced in high yield.

Each step of the disclosed process for synthesizing a normal alpha olefin can be conducted, independently, in any suitable reactor or vessel, non-limiting examples of which can include a fixed bed reactor, a stirred tank reactor, a plug flow reactor, a loop reactor, and a tubular reactor, including more than one reactor in series or in parallel, and including any combination of reactor types and arrangements. Each step, independently, can be performed batchwise or continuously.

Referring now to the FIGURE, the first reaction scheme illustrates the conversion of 1-butene to 1-decene in accordance with the disclosed process, and the second reaction scheme illustrates the conversion of ethylene to 1-hexene in accordance with the disclosed process. In the first reaction scheme, 1-butene is subjected to hydroformylation in the presence of carbon monoxide and hydrogen to form 1-pentanal, followed by subjecting 1-pentanal to decarbonylative olefination to form 4-nonene. Next, 4-nonene is subjected to isomerization-hydroformylation in the presence of carbon monoxide and hydrogen to form 1-decanal, which is subjected to hydrogenation to form 1-decanol, and finally the 1-decanol is subjected to dehydration to form 1-decene. Similarly, in the second reaction scheme, ethylene is subjected to hydroformylation in the presence of carbon monoxide and hydrogen to form propanal, followed by subjecting propanal to decarbonylative olefination to form 2-pentene. Next, 2-pentene is subjected to isomerization-hydroformylation in the presence of carbon monoxide and hydrogen to form 1-hexanal, which is subjected to hydrogenation to form 1-hexanol, and finally the 1-hexanol is subjected to dehydration to form 1-hexene.

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

Constructive Example 1

In accordance with the processes disclosed herein and the first reaction scheme in the FIGURE, Constructive Example 1 demonstrates a representative and non-limiting example of the conversion of 1-butene to 1-decene. First, 1-butene is combined with a rhodium-BiPhePhos catalyst system in a reactor. The elemental ratio of Rh:P is 1:1.1, and the molar ratio of the 1-butene to rhodium is 10,000:1. Carbon monoxide and hydrogen ($H_2$) are added to the reactor at a total pressure of 30 bar and a molar ratio of carbon monoxide to hydrogen of 1:1. The reactor is heated to 150° C. and the reactor contents are stirred for 1 hr to produce a first composition containing 1-pentanal. After cooling, an aldehyde composition containing 82 mol % 1-pentanal is separated from the first composition by distillation.

The aldehyde composition containing 1-pentanal is subjected to decarbonylative olefination by mixing the aldehyde composition in a reactor with a Pd/alumina catalyst containing 0.3 mol % palladium at a temperature of 180° C. for 2 hr. A second composition containing 4-nonene, carbon monoxide, and water is produced, and after cooling, an internal olefin composition containing 80 mol % 4-nonene is formed by venting the carbon monoxide and separating the 4-nonene from water by distillation or decantation.

The internal olefin composition containing 4-nonene is subjected to isomerization-hydroformylation in a manner similar to hydroformylation of 1-butene using a rhodium-BiPhePhos catalyst system discussed above (although a different catalyst can be used to improve selectivity). A second aldehyde composition containing 82 mol % 1-decanal is isolated by distillation.

In a reactor, the second aldehyde composition containing 1-decanal is mixed with a Cu/alumina catalyst containing 10 wt. % copper. Hydrogen ($H_2$) is added to the reactor at a total pressure of 50 bar and a molar ratio of hydrogen to 1-decanal of 1.5:1. The reactor is heated to 140° C. and the reactor contents are contacted at a liquid hourly space velocity (LHSV) of 18 $hr^{-1}$ to produce a fourth composition containing 1-decanol. After cooling, an alcohol composition containing 90 mol % 1-decanol is separated from the 1-decanal by distillation.

The alcohol composition containing 1-decanol is subjected to dehydration by mixing the alcohol composition with pre-calcined alumina at 300° C. for 2 hr to form a product composition containing 1-decene. After cooling, the product composition is purified to isolate an alpha olefin composition containing at least 60 mol % 1-decene by distillation.

Constructive Example 2

Using an analogous procedure to that of Constructive Example 1, Constructive Example 2 converts ethylene to 1-hexene as shown in the second reaction scheme in the FIGURE.

The invention is described herein with reference to numerous aspects and specific examples. Many variations will suggest themselves to those skilled in the art in light of the detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process comprising:
(i) subjecting a first normal alpha olefin having the structure $(C)_n$—C=C to hydroformylation in the presence of carbon monoxide and hydrogen to form a first composition comprising a first linear aldehyde having the structure $C(C)_{n+1}CH(=O)$;
(ii) subjecting the first linear aldehyde to decarbonylative olefination to form a second composition comprising a $C_{2n+5}$ linear internal olefin;
(iii) subjecting the linear internal olefin to isomerization-hydroformylation in the presence of carbon monoxide and hydrogen to form a third composition comprising a second linear aldehyde having the structure $C(C)_{2n+4}CH(=O)$; and
(iv-a) subjecting the second linear aldehyde to hydrogenation-dehydration to form a product composition comprising a second normal alpha olefin having the structure $(C)_{2n+4}$—C=C; or
(iv-b1) subjecting the second linear aldehyde to hydrogenation to form a fourth composition comprising a linear alcohol having the structure $C(C)_{2n+4}C(OH)$; and
(iv-b2) subjecting the linear alcohol to dehydration to form a product composition comprising a second normal alpha olefin having the structure $(C)_{2n+4}$—C=C;
wherein n is an integer from 0 to 30.

Aspect 2. The process defined in aspect 1, wherein n is an integer from 0 to 18.

Aspect 3. The process defined in aspect 1, wherein n is an integer from 0 to 6.

Aspect 4. The process defined in aspect 1, wherein the first normal alpha olefin comprises ethylene, propylene, 1-butene, 1-pentene, 1-hexene, 1-heptene, 1-octene, 1-nonene, 1-decene, 1-dodecene, 1-tetradecene, 1-hexadecene, 1-octadecene, or any combination thereof.

Aspect 5. The process defined in aspect 1, wherein the first normal alpha olefin comprises ethylene, propylene, 1-butene, 1-pentene, 1-hexene, 1-heptene, 1-octene, or any combination thereof.

Aspect 6. The process defined in aspect 1, wherein the first normal alpha olefin comprises ethylene, and the second normal alpha olefin comprises 1-hexene.

Aspect 7. The process defined in aspect 1, wherein the first normal alpha olefin comprises propylene, and the second normal alpha olefin comprises 1-octene.

Aspect 8. The process defined in aspect 1, wherein the first normal alpha olefin comprises 1-butene, and the second normal alpha olefin comprises 1-decene.

Aspect 9. The process defined in aspect 1, wherein the first normal alpha olefin comprises 1-pentene, and the second normal alpha olefin comprises 1-dodecene.

Aspect 10. The process defined in aspect 1, wherein the first normal alpha olefin comprises 1-hexene, and the second normal alpha olefin comprises 1-tetradecene.

Aspect 11. The process defined in aspect 1, wherein the first normal alpha olefin comprises 1-heptene, and the second normal alpha olefin comprises 1-hexadecene.

Aspect 12. The process defined in aspect 1, wherein the first normal alpha olefin comprises 1-octene, and the second normal alpha olefin comprises 1-octadecene.

Aspect 13. The process defined in any one of aspects 1-12, wherein the hydroformylation in step (i) utilizes a rhodium-based catalyst system.

Aspect 14. The process defined in aspect 13, wherein the rhodium-based catalyst system comprises rhodium and a phosphorus-containing ligand at an elemental ratio of Rh:P in any suitable range, e.g., from 1:1 to 1:15, from 1:2 to 1:10, or from 1:2 to 1:6.

Aspect 15. The process defined in aspect 14, wherein the phosphorus-containing ligand comprises BiPhePhos.

Aspect 16. The process defined in any one of aspects 13-15, wherein a molar ratio of the first normal alpha olefin to rhodium is in any suitable range, e.g., from 100:1 to 500,000:1, from 100:1 to 10,000:1, or from 100:1 to 1000:1.

Aspect 17. The process defined in any one of aspects 1-16, wherein a molar ratio of carbon monoxide to hydrogen in step (i) is in any suitable range, e.g., from 5:1 to 1:5, from 2:1 to 1:2, or from 1.5:1 to 1:1.5.

Aspect 18. The process defined in any one of aspects 1-17, wherein a source of carbon monoxide and hydrogen in step (i) is Syngas.

Aspect 19. The process defined in any one of aspects 1-18, wherein the hydroformylation in step (i) is conducted at any suitable pressure, e.g., from 5 to 70 bar, from 10 to 50 bar, or from 20 to 45 bar.

Aspect 20. The process defined in any one of aspects 1-19, wherein the hydroformylation in step (i) is conducted at any suitable temperature, e.g., from 80 to 200° C., from 80 to 160° C., or from 100 to 130° C.

Aspect 21. The process defined in any one of aspects 1-20, wherein the hydroformylation in step (i) is conducted in any suitable diluent, e.g., toluene, propylene carbonate, dimethylformamide, dodecane, or a combination thereof.

Aspect 22. The process defined in any one of aspects 1-21, wherein the first composition further comprises a diluent.

Aspect 23. The process defined in any one of aspects 1-22, further comprising a step of isolating an aldehyde composition comprising at least 85 mol %, at least 90 mol %, at least 93 mol %, or at least 96 mol % of the first linear aldehyde from the first composition prior to step (ii), via any suitable technique or any technique disclosed herein, e.g., extraction, filtration, evaporation, distillation, or any combination thereof.

Aspect 24. The process defined in any one of aspects 1-23, wherein the decarbonylative olefination in step (ii) utilizes a palladium-based catalyst system.

Aspect 25. The process defined in aspect 24, wherein the palladium-based catalyst system comprises Pd/hydrotalcite, Pd/alumina, Pd/gamma alumina, Pd/silica, Pd/carbon, Pd/magnesia, or a combination thereof, with any suitable amount of palladium, e.g., 0.01 to 10 mol %, from 0.05 to 5 mol %, or from 0.05 to 1 mol %.

Aspect 26. The process defined in any one of aspects 1-25, wherein the decarbonylative olefination in step (ii) is conducted at any suitable temperature, e.g., from 80 to 200° C., from 100 to 190° C., or from 150 to 180° C.

Aspect 27. The process defined in any one of aspects 1-26, wherein the second composition further comprises carbon monoxide and/or water.

Aspect 28. The process defined in any one of aspects 1-27, further comprising a step of isolating an internal olefin composition comprising at least 85 mol %, at least 90 mol %, at least 93 mol %, or at least 96 mol % of the linear internal olefin from the second composition prior to step (iii), via any suitable technique or any technique disclosed herein, e.g., extraction, filtration, evaporation, distillation, or any combination thereof.

Aspect 29. The process defined in any one of aspects 1-28, wherein the isomerization-hydroformylation in step (iii) utilizes a rhodium-based catalyst system.

Aspect 30. The process defined in aspect 29, wherein the rhodium-based catalyst system comprises rhodium and a phosphorus-containing ligand at an elemental ratio of Rh:P in any suitable range, e.g., from 1:1 to 1:15, from 1:2 to 1:10, or from 1:2 to 1:6.

Aspect 31. The process defined in aspect 30, wherein the phosphorus-containing ligand comprises BiPhePhos.

Aspect 32. The process defined in any one of aspects 29-31, wherein a molar ratio of the linear internal olefin to rhodium is in any suitable range, e.g., from 100:1 to 500,000:1, from 100:1 to 10,000:1, or from 100:1 to 1000:1.

Aspect 33. The process defined in any one of aspects 1-32, wherein a molar ratio of carbon monoxide to hydrogen in step (iii) is in any suitable range, e.g., from 5:1 to 1:5, from 2:1 to 1:2, or from 1.5:1 to 1:1.5.

Aspect 34. The process defined in any one of aspects 1-33, wherein a source of carbon monoxide and hydrogen in step (iii) is Syngas.

Aspect 35. The process defined in any one of aspects 1-34, wherein the isomerization-hydroformylation in step (iii) is conducted at any suitable pressure, e.g., from 5 to 70 bar, from 10 to 50 bar, or from 20 to 45 bar.

Aspect 36. The process defined in any one of aspects 1-35, wherein the isomerization-hydroformylation in step (iii) is conducted at any suitable temperature, e.g., from 80 to 200° C., from 80 to 160° C., or from 100 to 130° C.

Aspect 37. The process defined in any one of aspects 1-36, wherein the isomerization-hydroformylation in step (iii) is conducted in any suitable diluent, e.g., toluene, propylene carbonate, dimethylformamide, dodecane, or a combination thereof.

Aspect 38. The process defined in any one of aspects 1-37, wherein the third composition further comprises a diluent.

Aspect 39. The process defined in any one of aspects 1-38, further comprising a step of isolating a second aldehyde composition comprising at least 85 mol %, at least 90 mol %, at least 93 mol %, or at least 96 mol % of the second linear aldehyde from the third composition prior to step (iv-a) or (iv-b1), via any suitable technique or any technique disclosed herein, e.g., extraction, filtration, evaporation, distillation, or any combination thereof.

Aspect 40. The process defined in any one of aspects 1-39, wherein the hydrogenation in step (iv-b1) utilizes a copper-based catalyst system.

Aspect 41. The process defined in aspect 40, wherein the copper-based catalyst system comprise Cu/alumina with any suitable amount of copper, e.g., from 1 to 35 wt. 00 from 2 to 30 wt. %, or from 5 to 25 wt. %.

Aspect 42. The process defined in any one of aspects 1-41, wherein the hydrogenation in step (iv-b1) is conducted at any suitable temperature, e.g., from 80 to 200° C., from 90 to 190° C., or from 100 to 180° C.

Aspect 43. The process defined in any one of aspects 1-42, wherein the hydrogenation in step (iv-b1) is conducted at any suitable pressure, e.g., from 10 to 70 bar, from 20 to 50 bar, or from 25 to 45 bar.

Aspect 44. The process defined in any one of aspects 1-43, wherein the hydrogenation in step (iv-b1) is conducted at any suitable molar ratio of hydrogen to the second linear aldehyde, e.g., from 0.5:1 to 5:1, from 0.75:1 to 3:1, or from 1:1 to 2:1.

Aspect 45. The process defined in any one of aspects 1-44, further comprising a step of isolating an alcohol composition comprising at least 85 mol %, at least 90 mol %, at least 93 mol %, or at least 96 mol % of the linear alcohol from the fourth composition prior to step (iv-b2), via any suitable technique or any technique disclosed herein, e.g., extraction, filtration, evaporation, distillation, or any combination thereof.

Aspect 46. The process defined in any one of aspects 1-45, wherein the dehydration in step (iv-b2) utilizes an alumina-based catalyst system.

Aspect 47. The process defined in aspect 46, wherein the alumina is calcined at any suitable temperature, e.g., from 100 to 1200° C., from 250 to 1000° C., or from 400 to 600° C., prior to step (iv-b2).

Aspect 48. The process defined in any one of aspects 1-45, wherein the dehydration in step (iv-b2) utilizes a metal phosphate-based catalyst system.

Aspect 49. The process defined in any one of aspects 1-48, wherein the dehydration in step (iv-b2) is conducted at any suitable temperature, e.g., from 200 to 500° C., from 250 to 450° C., or from 300 to 400° C.

Aspect 50. The process defined in any one of aspects 1-49, wherein the product composition further comprises water.

Aspect 51. The process defined in any one of aspects 1-50, further comprising a step of purifying the product composition to isolate an alpha olefin composition comprising at least 85 mol %, at least 90 mol %, at least 93 mol %, or at least 96 mol % of the second normal alpha olefin, via any suitable technique or any technique disclosed herein, e.g., extraction, filtration, evaporation, distillation, or any combination thereof.

What is claimed is:

1. A process comprising:
   (i) subjecting a first normal alpha olefin having the structure $(C)_n$—C=C to hydroformylation in the presence of carbon monoxide and hydrogen to form a first composition comprising a first linear aldehyde having the structure $C(C)_{n+1}CH(=O)$;
   (ii) subjecting the first linear aldehyde to decarbonylative olefination to form a second composition comprising a $C_{2n+5}$ linear internal olefin;
   (iii) subjecting the linear internal olefin to isomerization-hydroformylation in the presence of carbon monoxide and hydrogen to form a third composition comprising a second linear aldehyde having the structure $C(C)_{2n+4}CH(=O)$; and
   (iv-a) subjecting the second linear aldehyde to hydrogenation-dehydration to form a product composition comprising a second normal alpha olefin having the structure $(C)_{2n+4}$—C=C; or
   (iv-b1) subjecting the second linear aldehyde to hydrogenation to form a fourth composition comprising a linear alcohol having the structure $C(C)_{2n+4}C(OH)$; and
   (iv-b2) subjecting the linear alcohol to dehydration to form a product composition comprising a second normal alpha olefin having the structure $(C)_{2n+4}$—C=C;
   wherein n is an integer from 0 to 30.

2. The process of claim 1, wherein n is an integer from 0 to 6.

3. The process of claim 1, wherein the first normal alpha olefin comprises ethylene, and the second normal alpha olefin comprises 1-hexene.

4. The process of claim 1, wherein the first normal alpha olefin comprises propylene, and the second normal alpha olefin comprises 1-octene.

5. The process of claim 1, wherein the first normal alpha olefin comprises 1-butene, and the second normal alpha olefin comprises 1-decene.

6. The process of claim 1, wherein the hydroformylation in step (i) utilizes a rhodium-based catalyst system.

7. The process of claim 6, wherein a molar ratio of the first normal alpha olefin to rhodium is in a range from 100:1 to 500,000:1.

8. The process of claim 1, wherein:
   a source of carbon monoxide and hydrogen in step (i) is Syngas; and
   the hydroformylation in step (i) is conducted in a diluent.

9. The process of claim 1, further comprising a step of isolating an aldehyde composition comprising at least 85 mol % of the first linear aldehyde from the first composition prior to step (ii).

10. The process of claim 1, wherein the decarbonylative olefination in step (ii) utilizes a palladium-based catalyst system.

11. The process of claim 10, wherein the palladium-based catalyst system comprises Pd/hydrotalcite, Pd/alumina, Pd/gamma alumina, Pd/silica, Pd/carbon, Pd/magnesia, or a combination thereof.

12. The process of claim 1, wherein:
   the second composition further comprises carbon monoxide and/or water; and
   the process further comprising a step of isolating an internal olefin composition comprising at least 85 mol % of the linear internal olefin from the second composition prior to step (iii).

13. The process of claim 1, wherein the isomerization-hydroformylation in step (iii) utilizes a rhodium-based catalyst system.

14. The process of claim 13, wherein the rhodium-based catalyst system comprises rhodium and a phosphorus-containing ligand at an elemental ratio of Rh:P in a range from 1:1 to 1:15.

15. The process of claim 14, wherein the phosphorus-containing ligand comprises BiPhePhos.

16. The process of claim 1, wherein a molar ratio of carbon monoxide to hydrogen in step (iii) is in a range from 5:1 to 1:5.

17. The process of claim 1, wherein the process comprises step (iv-b1) and step (iv-b2).

18. The process of claim 17, wherein the hydrogenation in step (iv-b1) utilizes a copper-based catalyst system.

19. The process of claim 17, wherein the hydrogenation in step (iv-b1) is conducted at a molar ratio of hydrogen to the second linear aldehyde in a range from 0.5:1 to 5:1.

20. The process of claim 17, wherein the dehydration in step (iv-b2) utilizes an alumina-based catalyst system or a metal phosphate-based catalyst system.

21. The process of claim 1, further comprising a step of purifying the product composition to isolate an alpha olefin composition comprising at least 85 mol % of the second normal alpha olefin.

* * * * *